(12) United States Patent
Coqueret et al.

(10) Patent No.: US 10,155,065 B2
(45) Date of Patent: Dec. 18, 2018

(54) PHOTOPOLYMERIZABLE LIQUID COMPOSITION

(71) Applicants: Laboratoires Urgo, Chenove (FR); Universite de Reims Champagne-Ardenne, Reims (FR); Centre National de la Recherche Scientifique, Paris (FR)

(72) Inventors: Xavier Coqueret, Reims (FR); Sadananda Das, West Bengal (IN); Stéphane Auguste, Ruffey les Echirey (FR)

(73) Assignees: LABORATORIES URGO, Chenove (FR); UNIVERSITE DE REIMS CHAMPAGNE-ARDENNE, Reims (FR); CENTER NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/104,193

(22) PCT Filed: Dec. 12, 2014

(86) PCT No.: PCT/FR2014/053318
§ 371 (c)(1),
(2) Date: Jun. 13, 2016

(87) PCT Pub. No.: WO2015/087020
PCT Pub. Date: Jun. 18, 2015

(65) Prior Publication Data
US 2017/0014544 A1      Jan. 19, 2017

(30) Foreign Application Priority Data
Dec. 13, 2013   (FR) .................... 13 62568

(51) Int. Cl.
| | |
|---|---|
| A61L 26/00 | (2006.01) |
| C08J 5/18 | (2006.01) |
| C08G 59/02 | (2006.01) |
| A61K 47/34 | (2017.01) |
| A61K 9/70 | (2006.01) |
| C08K 5/45 | (2006.01) |
| C08K 5/55 | (2006.01) |

(52) U.S. Cl.
CPC ........ *A61L 26/0014* (2013.01); *A61K 9/7007* (2013.01); *A61K 47/34* (2013.01); *A61L 26/0052* (2013.01); *A61L 26/0057* (2013.01); *C08G 59/027* (2013.01); *C08J 5/18* (2013.01); *C08K 5/45* (2013.01); *C08K 5/55* (2013.01)

(58) Field of Classification Search
CPC ............ A61L 26/0014; A61L 26/0052; A61L 26/0057; A61K 9/7007; A61K 47/34; C08G 59/1027; C08J 5/18; C08K 5/45; C08K 5/55
See application file for complete search history.

(56) References Cited

U.S. PATENT DOCUMENTS

| | | | | |
|---|---|---|---|---|
| 4,882,201 A | * | 11/1989 | Crivello ................. | C08G 59/68 427/515 |
| 5,849,460 A | | 12/1998 | Yoshinori et al. | |
| 5,992,314 A | * | 11/1999 | Lorenz ..................... | B32B 7/12 101/128.21 |
| 2002/0013380 A1 | * | 1/2002 | Chappelow .......... | C07D 493/10 522/14 |
| 2005/0165126 A1 | * | 7/2005 | Herlihy ................ | C07D 335/16 522/25 |
| 2009/0220436 A1 | * | 9/2009 | Anderson ............ | A61K 8/8152 424/45 |

FOREIGN PATENT DOCUMENTS

| | | |
|---|---|---|
| FR | 2972928 | 9/2012 |
| JP | 2001040068 | 2/2001 |
| JP | 2007126612 | 5/2007 |

OTHER PUBLICATIONS

Takahashi E; Yamase Y: "Photocurable epoxy resin composition—contg. acrylic ester and/or methacrylic ester and sensitiser with polymerisable substitute", Database WPI, Oct. 15, 1986, Thomson Scientific, London, GB; AN 1986-314219, XP002728939.
International Search Report and Written Opinion of the International Searching Authority, issued in connection with Application No. PCT/FR2014/053318, dated Feb. 24, 2015, 8 pages.

* cited by examiner

*Primary Examiner* — Doan T Phan
(74) *Attorney, Agent, or Firm* — McAndrews, Held & Malloy, Ltd.

(57) ABSTRACT

The subject matter of the present invention is a photopolymerizable liquid composition comprising at least one epoxidized polybutadiene prepolymer, at least one cationic photoinitiator, and at least one thioxanthone-derived photosensitizer, which can, for example, be in the form of a liquid dressing. The subject matter of the invention is also a process for obtaining a polymerized film from said photopolymerizable liquid composition, characterized in that said composition is applied to tissues such as the skin, the skin appendages or the mucous membranes so as to form a uniform liquid film, and the film thus obtained is subjected to ultraviolet radiation, preferably ultraviolet-visible radiation having a wavelength of between 380 and 405 nm, preferably between 385 and 395 nm.

12 Claims, 1 Drawing Sheet

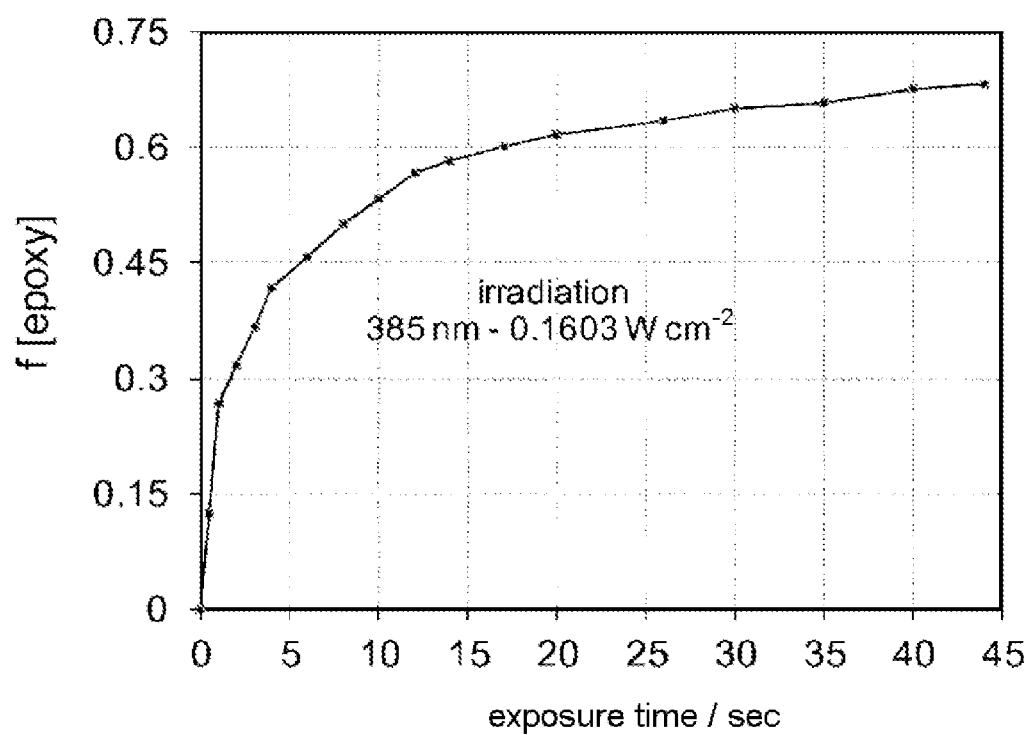

PHOTOPOLYMERIZABLE LIQUID COMPOSITION

The present application is filed pursuant to 35 U.S.C. 371 as a U.S. National Phase application of International Patent Application No. PCT/FR2014/053318, which was filed Dec. 12, 2014, claiming the benefit of priority to France Patent Application No. 13 62568(FR), which was filed on Dec. 13, 2013. The entire text of the aforementioned applications is incorporated herein by reference in its entirety.

The subject of the present invention is the use of a photopolymerizable liquid composition comprising at least one epoxidized polybutadiene prepolymer, at least one cationic photoinitiator, and at least one photosensitizer derived from thioxanthone, phenothiazine, fluoflavin, anthracene, curcumin, dithienothiophene or xanthene-based or fluorone-based dyes, preferably a thioxanthone derivative, for application thereof to tissues such as the the skin, the skin appendages (the nails or the hair) and/or the mucous membranes. The subject of the invention is also a process for obtaining a polymerized film on tissues such as the skin, the skin appendages or the mucous membranes from said photopolymerizable liquid composition.

Film-forming compositions are intended to be applied, with or without applicator, to tissues such as the skin, the skin appendages or the mucous membranes. They can also be used as a liquid dressing, and are then applied to wounds, lesions, scars, burnt tissues and/or skin complaints. They are generally liquid on application and conventionally contain a film-forming polymer dissolved in a volatile solvent, typically water or an alcohol. Evaporation of the solvent then allows the formation of a protective solid film.

However, water-based film-forming compositions have the drawback of having quite a long drying time, this being all the longer the thicker the desired film. Film-forming compositions based on alcohol or on other organic solvents can make it possible to obtain significantly reduced drying times, but can be painful when they are applied to wounds or lesions, and are thus not very suitable for a use of dressing type.

In addition, solidified films formed by means of these compositions based on film-forming polymers usually have limited mechanical properties, in particular in terms of elasticity and of breaking strength.

Film-forming compositions have been formulated and tested in the electronics field, but their composition or their use is not suitable for applications on tissues such as the skin, the skin appendages or the mucous membranes. Thus, the compositions described in patent applications JP 2001 040068 and U.S. Pat. No. 5,849,460 form films polymerized by means of mercury lamps, which are incompatible with application to tissues, in particular the skin. Applications JP S61 231022 and JP S61 213217 describe compositions comprising Bisphenol A which is known for its toxicity. Finally, the composition described in application JP 2007 126612 uses monomers of which the application to tissues, in particular to lesioned skin, is painful and unsuitable for use as a dressing.

There is therefore a need for new non-cytotoxic film-forming compositions capable of rapidly forming, in-situ, solid films resistant to breaking, having good properties of adhesion to tissues such as the skin, the skin appendages or the mucous membranes, and good elasticity properties.

The applicant has found, surprisingly, that it is possible to form such films on tissues such as the skin, the skin appendages or the mucous membranes, said films having excellent breaking strength, adhesion and elasticity properties, by means of a particular photopolymerizable liquid composition.

The subject of the invention is thus, according to a first aspect, the use of a photopolymerizable liquid composition comprising at least one epoxidized polybutadiene prepolymer, at least one cationic photoinitiator, and at least one photosensitizer derived from thioxanthone, phenothiazine, fluoflavin, anthracene, curcumin, dithienothiophene, or xanthene-based or fluorone-based dyes, preferably a thioxanthone derivative, for application thereof to tissues such as the skin, the skin appendages and/or the mucous membranes.

According to a second aspect, the subject of the invention is also a process for obtaining a polymerized film on tissues such as the skin, the skin appendages or the mucous membranes from said photopolymerizable liquid composition.

A more detailed description of certain preferential embodiments of the invention is given below.

DETAILED DESCRIPTION OF THE INVENTION

According to a first aspect, the present invention relates to the use of a photopolymerizable liquid composition comprising:
- at least one epoxidized polybutadiene prepolymer,
- at least one cationic photoinitiator, and
- at least one photosensitizer derived from thioxanthone, phenothiazine, fluoflavin, anthracene, curcumin or dithienothiophene, preferably a thioxanthone derivative, for application thereof to tissues such as the skin, the skin appendages and/or the mucous membranes.

The subject of the invention is also a process for obtaining a polymerized film on tissues such as the skin, the skin appendages and/or the mucous membranes, from the photopolymerizable liquid composition previously described, characterized in that:

i. said composition is applied to tissues such as the skin, the skin appendages or the mucous membranes so as to form a uniform film, ii. the film obtained in step i. is subjected to ultraviolet (UV) radiation, preferably UV-visible radiation having a wavelength of between 380 and 405 nm, preferably between 385 and 395 nm.

In particular, the photopolymerizable liquid composition according to the invention is physiologically acceptable, i.e. non-toxic and capable of being applied to tissues such as the skin, the skin appendages or the mucous membranes of human beings or of animals and allows the formation of a biocompatible polymerized film.

Epoxidized Polybutadiene Prepolymer

The photopolymerizable liquid composition according to the invention comprises at least one epoxidized polybutadiene prepolymer. The epoxidized polybutadiene prepolymer is a low-molecular-weight liquid polybutadiene functionalized with at least one cationically polymerizable epoxide group.

Indeed, the applicant has demonstrated that, by using an epoxidized polybutadiene prepolymer rather than the conventional low-molecular-weight epoxide monomers, the photopolymerizable liquid composition according to the invention can be used on open wounds without causing an undesirable painful sensation (burning, stinging, etc.) when it is applied. The use of this prepolymer makes it possible, moreover, to avoid the diffusion of monomers into the wounds when the composition is applied to lesions, burnt tissues and/or skin complaints.

According to one particular embodiment, the epoxidized polybutadiene prepolymer has at least one of the following properties:

a molecular weight of between 500 and 10 000 g/mol, preferentially of between 1000 and 5000 g/mol, and more preferentially of between 1200 and 2500 g/mol, a dynamic viscosity at 25° C. (298K) of between 0.1 and 100 Pa·s, preferentially of between 2.5 and 50 Pa·s, and more preferentially of between 5 and 25 Pa·s, and an epoxide number of between 0.05 and 1 mol/100 g, preferentially of between 0.1 and 0.5 mol/100 g, and more preferentially of between 0.15 and 0.45 mol/100 g.

The epoxide number is the number of moles of epoxide groups per 100 grams of prepolymer. The epoxide number can in particular be measured according to standard NF EN ISO 3001 (May 1999, Plastics—Epoxide compositions—Determination of epoxy equivalent).

Epoxidized polybutadiene prepolymers that may be suitable in the context of the present application are in particular the products sold by the company Cray Valley under the names Poly BD605E and Poly BD600E.

According to one particular embodiment, the epoxidized polybutadiene prepolymer is present in a content of between 5 and 99.8% by weight, preferentially of between 10 and 90% by weight, even more preferentially between 15 and 80% by weight, relative to the total weight of the photopolymerizable liquid composition.

Cationic Photoinitiator

The photopolymerizable liquid composition according to the invention also comprises at least one cationic photoinitiator.

According to one preferred embodiment, the cationic photoinitiator is an onium salt sensitive to UV or UV-visible radiation and makes it possible to initiate the photopolymerization reaction.

It can in particular be chosen from the group comprising diazonium salts, halonium salts and in particular iodonium salts, sulfonium salts, sulfoxonium salts and selenonium salts.

Cationic photoinitiators that may be suitable in the context of the present application are in particular aryldiazonium salts, aryliodonium salts, diaryliodonium salts, alkylaryliodonium salts, arylsulfonium salts, triarylsulfonium salts, diarylbromonium salts, triarylselenonium salts, thioxanthonium salts, triarylsulfoxonium salts, aryloxysulfoxonium salts, dialkylacylsulfoxonium salts, dialkylphenacylsulfonium salts and dialkyl-4-hydroxyphenylsulfonium salts.

According to one particular embodiment, the cationic photoinitiator is chosen from bis(4-tert-butylphenyl)iodonium perfluoro-1-butanesulfonate, bis(4-tert-butylphenyl)iodonium p-toluenesulfonate, bis(4-tert-butylphenyl)iodonium triflate, boc-methoxyphenyldiphenylsulfonium triflate, (4-bromophenyl)diphenylsulfonium triflate, (tert-butoxycarbonyl methoxynaphthyl)diphenylsulfonium triflate, (4-tert-butylphenyl)diphenylsulfonium triflate, diphenyliodonium 9,10-dimethoxyanthracene-2-sulfonate, (p-isopropylphenyl) (m-methylphenyl)iodonium tetrakis(pentafluorophenyl)borate, diphenyliodonium hexafluorophosphate, diphenyliodonium nitrate, diphenyliodonium perfluoro-1-butanesulfonate, diphenyliodonium p-toluenesulfonate, diphenyliodonium triflate, (4-fluorophenyl)diphenylsulfonium triflate, N-hydroxynaphthalimide triflate, N-hydroxy-5-norbornene-2,3-dicarboximide perfluoro-1-butanesulfonate, (4-iodophenyl)diphenylsulfonium, (4-methoxyphenyl)diphenylsulfonium triflate, 2-(4-methoxystyryl)-4,6-bis(trichloromethyl)-1,3,5-triazine, (4-methylphenyl)diphenylsulfonium, (4-methylthiophenyl)methyl phenyl sulfonium triflate, 1-naphthyl diphenylsulfonium triflate, (4-phenoxyphenyl)diphenylsulfonium triflate, (4-phenylthiophenyl)diphenylsulfonium triflate, triarylsulfonium hexafluoroantimonate salts, triarylsulfonium hexafluorophosphate salts, triphenylsulfonium perfluoro-1-butanesulfonate, triphenylsulfonium triflate, tris(4-tert-butylphenyl) sulfonium perfluoro-1-butanesulfonate, tris(4-tert-butylphenyl)sulfonium triflate, 4-(1-methylethyl) phenyl 4-methylphenyliodonium tetrakis(pentafluorophenyl)borate (or diaryl iodonium tetrafluoroborate), hexafluoroarsenates, and mixtures thereof.

According to one preferential embodiment, the cationic photoinitiator is chosen from diaryliodonium salts, and is preferably 4-(1-methylethyl) phenyl 4-methylphenyliodonium tetrakis(pentafluorophenyl)borate (or diaryl iodonium tetrafluoroborate).

According to one particular embodiment, the cationic photoinitiator is present in a content of between 0.1 and 10% by weight, preferentially between 0.25 and 5% by weight, even more preferentially between 0.5 and 1.5% by weight, relative to the total weight of the photopolymerizable liquid composition.

Photosensitizer Derived from Thioxanthone, Phenothiazine, Fluoflavin, Anthracene, Curcumin, Dithienothiophene, or Xanthene-Based or Fluorone-Based Dyes.

The photopolymerizable liquid composition according to the invention also comprises at least one photosensitizer derived from thioxanthone, phenothiazine, fluoflavin, anthracene, curcumin, dithienothiophene, or xanthene-based or fluorone-based dyes.

For the purposes of the present application, the term "photosensitizer" is intended to mean a compound which passes into the excited state by exposure to UV, visible or UV-visible radiation, preferably UV-visible or visible radiation, and interacts directly with the cationic photoinitiator by energy or electron transfer, or else indirectly by generating, in-situ, radical entities which result in a reduction of the cationic photoinitiator, all of these processes releasing cationic entities or protons responsible for the initiating of the cationic polymerization of the epoxides.

When it is introduced into the photopolymerizable liquid compositions according to the invention, the photosensitizer derived from thioxanthone, phenothiazine, fluoflavin, anthracene, curcumin, dithienothiophene, or xanthene-based or fluorone-based dyes confers on the composition a photobleaching property, i.e. it allows UV, visible or UV-visible radiation to penetrate through the entire thickness of the liquid composition to be polymerized, thus promoting rapid initiating of deep photopolymerization of the composition according to the invention. The film obtained is thus uniformly polymerized over its entire thickness, thereby giving it excellent breaking strength, adhesion and elasticity properties.

According to one particularly preferred embodiment, the photosensitizer derived from thioxanthone, phenothiazine, fluoflavin, anthracene, curcumin, dithienothiophene, or xanthene-based or fluorone-based dyes is sensitive to UV-visible radiation of which the wavelength is between 200 and 500 nm, preferably between 300 and 450 nm, and even more preferentially between 380 and 405 nm.

This preferred range of wavelengths advantageously makes it possible not to damage the tissues such as the skin, the skin appendages or the mucous membranes to which the photopolymerizable liquid composition is applied, during the photopolymerization.

According to one particular embodiment, the photosensitizer derived from thioxanthone, phenothiazine, fluoflavin, anthracene, curcumin, dithienothiophene, or xanthene-based or fluorone-based dyes is present in a content of between 0.1 and 10% by weight, preferentially between 0.25 and 5% by weight, more preferentially between 0.5 and 1.5% by weight, relative to the total weight of the photopolymerizable liquid composition.

According to another particular embodiment, the ratio between the content of photosensitizer derived from thioxanthone, phenothiazine, fluoflavin, anthracene, curcumin, dithienothiophene, or xanthene-based or fluorone-based dyes and the content of cationic photoinitiator in the photopolymerizable liquid composition of the invention is between 0.1 and 1, preferentially between 0.5 and 0.75, more preferentially between 0.6 and 0.7.

A wide range of xanthene-based or fluorone-based dyes can be used in the present invention. Some examples include methylene blue, rhodamine B, Rose Bengal, 3-hydroxy-2,4,5,7-tetraiodo-6-fluorone, 5,7-diiodo-3-butoxy-6-fluorone, erythrosine B, eosin B, ethyl erythrosine, acridine orange, and 6'-acetyl-4,5,6,7-tetrachloro-2',4',5',6',7'-tetraiodofluorescein (RBAX).

The photosensitizer is preferably a thioxanthone derivative.

The thioxanthone-derived photosensitizer is a compound of formula (I):

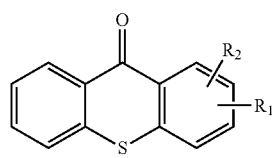

(I)

wherein $R_1$ and $R_2$ are, independently of one another, chosen from the group consisting of a hydrogen, a halogen, and a substituted or unsubstituted, linear or branched carbon-based chain comprising from two to twenty-two carbon atoms, which can be interrupted with one or more oxygen atoms, and can include saturated or unsaturated carbon bonds.

The $R_1$ and $R_2$ groups can include, for example, alkyl, alkenyl, alkynyl, alkoxy, alkenoxy, alkynoxy groups and similar groups, which are linear or branched, and which may be functionalized with heteroatomic groups or hydrocarbon-based radicals bearing heteroatomic functions including hydroxyl, nitro or thioether groups or other pharmaceutically or cosmetically acceptable functional groups.

According to one particular embodiment, the thioxanthone-derived photosensitizer is chosen from 1-chloro-4-propoxythioxanthone, 2-chlorothioxanthone, 2,4-diethylthioxanthone, isopropylthioxanthone, thioxanthone, and mixtures thereof.

According to one preferential embodiment, the thioxanthone-derived photosensitizer is isopropylthioxanthone.

Second Prepolymer Different than the Epoxidized Polybutadiene

The photopolymerizable liquid composition according to the invention can also comprise a second prepolymer, different than the epoxidized polybutadiene.

The addition of a second prepolymer makes it possible in particular to adjust the viscosity of the epoxidized polybutadiene-based composition and/or the physicochemical properties of the film once polymerized, for example its properties of elasticity and of adhesion to tissues such as the skin, the skin appendages or the mucous membranes.

The second prepolymer is preferably a vegetable oil of natural origin functionalized with at least one cationically polymerizable epoxide group.

According to one particular embodiment, the second prepolymer is chosen from epoxidized almond oil, epoxidized peanut oil, epoxidized argan oil, epoxidized rapeseed oil, epoxidized coconut oil, epoxidized linseed oil, epoxidized corn oil, epoxidized mustard oil, epoxidized olive oil, epoxidized palm oil, epoxidized grapeseed oil, epoxidized castor oil, epoxidized sesame oil, epoxidized soybean oil, epoxidized sunflower oil, and mixtures thereof.

According to one preferential embodiment, the second prepolymer is epoxidized soybean oil.

The second prepolymer can in particular be introduced in a content of between 20% and 80% by weight, preferentially between 25% and 60% by weight, more preferentially between 30% and 50% by weight, relative to the total weight of the epoxidized polybutadiene prepolymer and of the second prepolymer.

Hydrogen-Donor Compound

The photopolymerizable liquid composition according to the invention can also comprise a hydrogen-donor compound. Advantageously, the hydrogen-donor compound can in particular make it possible to increase the photopolymerization reaction kinetics.

The hydrogen-donor compound may be a primary, secondary or tertiary alcohol, in particular chosen from n-propanol, isopropanol, benzyl alcohol, t-butanol, and mixtures thereof.

The amount of the hydrogen-donor compound can be between 1% and 10% by weight, preferentially between 2% and 8% by weight, and more preferentially between 3% and 5% by weight, relative to the total weight of the photopolymerizable liquid composition.

Additives

The photopolymerizable liquid composition according to the invention may also comprise one or more additives, preferably non-basic additives. This is because basic additives are capable of impairing the photopolymerization of the composition according to the invention by interacting with the active centers ensuring propagation of the cationic polymerization.

The additives that can be introduced into the photopolymerizable liquid composition according to the invention can in particular be chosen from fragrances, flavorings, dyes, pigments, matting agents, rheological agents, preservatives, vitamins, essential oils and active agents, in particular chosen from antibacterial agents, antiseptics, antivirals, antifungal agents, painkillers, anti-inflammatories, agents which promote healing, moisturizing agents, depigmenting agents, keratolytic agents, restructuring active agents, anesthetics, and mixtures thereof.

In particular, the active agents that can be introduced into the composition according to the invention can be chosen from:
antibacterials, such as polymyxin B, penicillins (amoxycillin), clavulanic acid, tetracyclines, minocycline, chlorotetracycline, aminoglycosides, amikacin, gentamicin, neomycin, silver and salts thereof (silver sulfadiazine), probiotics;

antiseptics, such as sodium mercurothiolate, eosin, chlorhexidine, phenylmercuric borate, aqueous hydrogen peroxide, Dakin's solution, triclosan, biguanide, hexamidine, thymol, lugol, povidone iodine, merbromin, benzalkonium chloride and benzethonium chloride, ethanol, isopropanol;

antivirals, such as [gamma] aciclovir, famciclovir, ritonavir;

antifungals, such as polyenes, nystatin, amphotericin B, natamycin, imidazole compounds (miconazole, ketoconazole, clotrimazole, econazole, bifonazole, butoconazole, fenticonazole, isoconazole, oxiconazole, sertaconazole, sulconazole, thiabendazole, tioconazole), triazole compounds (fluconazole, itraconazole, ravuconazole, posaconazole, voriconazole), allylamines, terbinafine, [gamma] amorolfine, naftifine, butenafine;

flucytosine (antimetabolite), griseofulvin, caspofungin or micafungin; painkillers such as paracetamol, codeine, dextropropoxyphene, tramadol, morphine and its derivatives, corticoids and derivatives;

anti-inflammatories such as glucocorticoids, non-steroidal anti-inflammatories, aspirin, ibuprofen, ketoprofen, flurbiprofen, diclofenac, aceclofenac, ketorolac, meloxicam, piroxicam, tenoxicam, naproxene, indomethacin, naproxcinod, nimesulide, celecoxib, etoricoxib, parecoxib, rofecoxib, valdecoxib, phenylbutazone, niflumic acid or mefenamic acid;

active agents which promote healing, such as retinol, vitamin A, vitamin E, N-acetylhydroxyproline, *Centella asiatica* extracts, papain, silicones, thyme, niaouli, rosemary and sage essential oils, hyaluronic acid, synthetic polysulfated oligosaccharides having 1 to 4 monosaccharide units, such as sucrose octasulfate potassium salt, sucrose octasulfate silver salt or sucralfate, metformin, aspirin, allantoin; moisturizing agents such as hyaluronic add, urea, glycerol, fatty acids, aquaporin modulators, vegetable oils, chitosan, certain sugars, including sorbitol, butters and waxes;

depigmenting agents such as kojic acid (Kojic Acid SL® Quimasso (Sino Lion)), arbutin (Olevatin® Quimasso (Sino Lion)), the mixture of sodium palmitoylpropyl and European water lily extract (Sepicalm® Seppic), undecylenoylphenylalanine (Sepiwhite®—Seppic), the licorice extract obtained by fermentation of *Aspergillus* and ethoxydiglycol (Gatuline Whitening®—Gattefossé), octadecenedioic acid (ODA White®—Sederma), alpha-arbutin (Alpha-arbutin®, SACI-CFPA (Pentapharm)), the aqueous extract of Arctophylos uva-ursi leaves (Melfade-J®—SACI-CFPA (Pentapharm)), the complex plant mixture Gigawhite® (SACI-CFPA (Alpaflor)), diacetyl boldine (Lumiskin®—Sederma), the satsuma extract (Melaslow®—Sederma), the mixture of lemon extract enriched in citric acid and of cucumber extract (Uninontan®U-34—Unipex), the mixture of *Rumex occidentalis* extract and of vitamin C (Tyrostat® 11—Unipex), oligopeptides (Melanostatin 5®—Unipex), kojic dipalmitate (KAD-15®—Quimasso (Sino Lion)), the complex of natural origin Vegewhite® from LOW, wheat germ extracts (Clariskin® II—Silab), pethyldiamine triacetate (EDTA); keratolytic agents, such as salicylic acid, zinc salicylate, ascorbic acid, α-hydroxylated acids (glycolic, lactic, malic, citric or tartaric acid), silver maple, sour cherry or tamarind extracts, urea, the topical retinoid Keratoline® (Sederma), the proteases obtained by fermentation of Bacillus subtilis, the product Linked-Papain® (SACI-CFPA), or papain (proteolytic enzyme from the papaya fruit);

restructuring active agents (for example restructuring active agents for the skin appendages), such as silica derivatives, vitamin E, chamomile, calcium, horsetail extract or silk lipester; anesthetics such as benzocaine, lidocaine, dibucaine, pramoxine hydrochloride, bupivacaine, mepivacaine, p ilocaine or etidocaine.

According to one particular embodiment, the photopolymerizable liquid composition is in the form of a liquid dressing.

Indeed, the composition according to the invention makes it possible to obtain a polymerized film having properties that are particularly advantageous for use as a liquid dressing, i.e. a film which adheres to the skin for several hours, which does not exhibit any surface tackiness and which withstands water, in particular withstands several washes of the hands.

The subject of the present invention is also a photopolymerizable liquid composition as described above, comprising:

at least one epoxidized polybutadiene prepolymer,
at least one cationic photoinitiator, and
at least one photosensitizer derived from thioxanthone, phenothiazine, fluoflavin, anthracene, curcumin or dithienothiophene, preferably a thioxanthone derivative, for application thereof to a wound and/or lesioned skin.

According to another aspect, the subject of the invention is a process for obtaining a polymerized film on tissues such as the skin, the skin appendages and/or the mucous membranes, from the photopolymerizable liquid composition described above, characterized in that:

i. said composition is applied to tissues such as the skin, the skin appendages or the mucous membranes so as to form a uniform liquid film, ii. the film obtained in step i. is subjected to UV radiation, preferably UV-visible radiation having a wavelength of between 380 and 405 nm, preferably between 385 and 395 nm.

According to one particular embodiment, the UV radiation is carried out at a fixed wavelength, the value of which is chosen between 385 and 395 nm.

Advantageously, the process according to the invention makes it possible to easily and rapidly obtain a polymerized film having excellent breaking strength, adhesion and elasticity properties. In particular, the choice of an epoxidized polybutadiene prepolymer makes it possible to rapidly obtain a polymerized film since no inhibitory effect on the photopolymerization by oxygen is experienced.

Furthermore, the wavelength range chosen advantageously makes it possible not to damage the tissues such as the skin, the skin appendages or the mucous membranes to which the photopolymerizable liquid composition is applied, during the photopolymerization.

According to one preferred embodiment, the uniform film formed in step i. has a thickness of greater than 500 nm, preferably of between 1 and 300 µm, more preferentially of between 2 and 200 µm.

According to one particular embodiment, the film obtained in step i. is subjected to UV radiation, preferably UV-visible radiation, for a period of time sufficient to obtain at least 50%, preferably at least 75%, conversion of the epoxide groups. Indeed, the polymerized films obtained from the compositions according to the invention have the desired physicochemical properties when the conversion of the epoxide groups is at least 50% and preferably at least 75%. The conversion of the epoxide groups is established on the basis of an FTIR spectroscopy experiment. It is calculated by measuring the initial height ($h_0$) and the height at each instant ($h_t$) of the absorption peaks characteristic of the epoxide groups and by applying the formula below:

conversion=1−($h_t/h_0$)

The film obtained in step i. is thus subjected to UV radiation, preferably UV-visible radiation, for a period of between 5 seconds and 60 minutes, preferentially between 5 seconds and 30 minutes, more preferentially between 5 seconds and 10 minutes. These exposure time ranges advantageously make it possible not to damage the tissues such as the skin, the skin appendages or the mucous membranes to which the photopolymerizable liquid composition is applied.

According to one particular embodiment, the exposure to UV radiation, preferably UV-visible radiation, is carried out continuously.

According to one particular embodiment, the exposure to UV radiation, preferably UV-visible radiation, is carried out batchwise.

The present invention is illustrated in greater detail in the nonlimiting examples described hereinafter.

EXAMPLES

Example 1

Preparation of a Photopolymerizable Liquid Composition

A photopolymerizable liquid composition comprising the compounds described in the table below was prepared:

| Compound | (% by weight) |
| --- | --- |
| Epoxidized polybutadiene prepolymer (Poly BD605E) | 97.5 |
| Diaryl iodonium tetrakis(pentafluorophenyl)borate (Bluesil PI2074) | 1 |
| Isopropylthioxanthone (ITX) | 1.5 |

The epoxidized polybutadiene prepolymer (Poly BD605E) is sold by Sartomer.

The diaryl iodonium borate (Bluesil PI2074) is 4-(1-methylethyl) phenyl 4-methylphenyliodonium tetrakis(pentafluorophenyl)borate sold by BlueStar.

The isopropylthioxanthone (ITX) used is sold by Aldrich.

All the compounds were mixed until a homogeneous solution was obtained. The solution thus obtained was then stored at ambient temperature and was protected against light until its use.

Study of the Conversion of the Epoxide Groups of the Photopolymerizable Liquid Composition Prepared The conversion of the epoxide groups of the photopolymerizable liquid composition is monitored by FTIR spectroscopy (Vertex 70 spectrometer, Bruker). The progression thereof is monitored continuously by verifying the disappearance of the absorption peak characteristic of the epoxide group of the Poly BD605E at 890 cm$^{-1}$.

The conversion of the epoxide groups of the composition is calculated as described above.

The photopolymerizable liquid composition is prepared according to the following protocol. Said composition is deposited on a silicon plate, attached to an aluminum support. The thickness of the liquid film deposited is 20 μm.

The composition is then exposed, under air and at ambient temperature, to UV radiation, preferably UV-visible radiation, having a wavelength of 385 nm emitted by an LED-LC3 (Hamamatsu Photonics K.K.) positioned at a distance of 7.5 cm from the composition and with a surface power density of 0.1603 W·cm$^{-2}$. The exposure is carried out continuously for a period of 50 seconds.

The figure shows the progression of the conversion of the epoxide groups of the composition (as %) as a function of the exposure time.

Under the conditions of the experiment, after 50 seconds of exposure, the conversion of the epoxide groups is greater than 81%. The film thus obtained is elastic, adheres to the skin, exhibits no surface tackiness, withstands water, and has good breaking strength.

Example 2

Study of the Addition of a Second Prepolymer to a Photopolymerizable Liquid Composition A photopolymerizable liquid composition comprising the compounds described in the table below was prepared as in example 1.

| Compound | % by weight |
| --- | --- |
| Poly BD605E | 58.5 |
| Epoxidized soybean oil (ESO) | 39 |
| Bluesil PI2074 | 1 |
| ITX | 1.5 |

The epoxidized soybean oil (ESO) is a second prepolymer sold by Ackross.

The conversion of the epoxide groups of this composition was studied according to a protocol equivalent to that described in example 1.

However, the disappearance of the absorption peak characteristic of the epoxide group of the epoxidized soybean oil is monitored at 823 cm$^{-1}$. Furthermore, the exposure time is 600 seconds.

Under the conditions of the experiment, after 600 seconds of exposure, the conversion of the epoxide groups is greater than 80%.

It appears that the addition of epoxidized soybean oil makes it possible to obtain a film having properties of elasticity and of adhesion to the skin that are further improved compared with those of the composition of example 1.

Furthermore, as for the film obtained with the composition of example 1, the film obtained with the composition of example 2 exhibits no surface tackiness, withstands water, and has good breaking strength.

Example 3

Study of the Addition of a Hydrogen-Donor Compound to a Photopolymerizable Liquid Composition A photopolymerizable liquid composition comprising the compounds described in the table below was prepared as in example 1.

| Compound | % by weight |
| --- | --- |
| Poly BD605E | 92.5 |
| Bluesil PI2074 | 1 |

| Compound | % by weight |
|---|---|
| ITX | 1.5 |
| Benzyl alcohol | 5 |

Benzyl alcohol is used here as a hydrogen-donor compound; it is sold by Aldrich. Before it is used, it is stored on molecular sieves in order to reduce the moisture content.

The conversion of the epoxide groups of this composition was studied according to a protocol identical to that described in example 1.

Under the conditions of the experiment, after 50 seconds of exposure, the conversion of the epoxide groups is greater than 84%. The polymerization is therefore accelerated by adding benzyl alcohol. Furthermore, as for example 1, the film obtained with the composition of example 3 is elastic, adheres to the skin, exhibits no surface tackiness, withstands water, and has good breaking strength.

Example 4

Study of the Effect of the Thioxanthone-Derived Photosensitizer on the Photobleaching Phenomenon, at Various Photopolymerizable Film Thicknesses A photopolymerizable liquid composition identical to that of example 1 was prepared.

The photobleaching of the isopropylthioxanthone was studied by continuous measurement of the absorbance at 385 nm of the composition prepared, in a UV-visible spectrophotometer.

The protocol followed is the following. Samples, of different thicknesses (of between 15 and 200 μm), of the composition prepared were first placed between two thin glasses (150 μm). They were then exposed to UV-visible radiation having a wavelength of 385 nm emitted by an LED-LC3 (Hamamatsu Photonics K.K.) positioned at a distance of 6 cm and with a surface power density of 0.1807 W·cm$^{-2}$. The exposure is carried out continuously for a period of 20 seconds.

Under the conditions of the experiment, and after the 20 seconds of exposure, the degree of progression of the photobleaching is between 0.95 and 1 for all the samples. The photobleaching phenomenon allows deep initiating of the photopolymerization. A degree of progression of the photobleaching of between 0.95 and 1 obtained under the present conditions therefore allows uniform polymerization of the film throughout its thickness.

Example 5

A photopolymerizable liquid composition comprising the compounds described in the table below was prepared as in example 1 (replacement of ITX with DETX and epoxidized soybean oil with epoxidized linseed oil).

| Compound | % by weight |
|---|---|
| Poly BD605E | 58.5 |
| Bluesil PI2074 | 1 |
| 2,4-diethyl-9H-thioxanthen-9-one (Genocure DETX from Rahn) | 1.5 |
| Epoxidized linseed oil | 39 |

Example 6

A photopolymerizable liquid composition comprising the compounds described in the table below was prepared as in example 1 (replacement of ITX with curcumin and of epoxidized soybean oil with epoxidized linseed oil).

| Compound | % by weight |
|---|---|
| Poly BD605E | 58.5 |
| Bluesil PI2074 | 1 |
| Curcumin | 1.5 |
| Epoxidized linseed oil | 39 |

Example 7

Test for Breaking Strength of the Compositions of Examples 1, 2 and 3

The compositions of examples 1, 2 and 3 are spread so as to have a thickness of 55 μm on a polyester film having a siliconized face. These compositions are then subjected to UV-A crosslinking (wavelengths of between 320 and 400 nm) at a power of 3.166 Watts/cm$^2$ for 15 seconds.

Film samples 70 mm long and 15 mm wide are cut out.

The samples are decomplexed from the support on which they were prepared.

These films are then subjected to a tensile force using a dynamometer. The films are placed between the jaws of the dynamometer so as to have 50 mm between each jaw. They are subjected to a force of 100 N at a speed of 300 mm/min until breaking.

The results of these tests appear in the following table:

|  | Mean elongation at break (%) | Mean breaking force (N/cm) |
|---|---|---|
| Formulation according to example 1 | 11.6 | 13.57 |
| Formulation according to example 2 | 22.9 | 2.79 |
| Formulation according to example 3 | 50.6 | 8.09 |

Example 8

Application of the Photopolymerizable Liquid Composition to the Skin

The photopolymerizable liquid composition of example 1 was applied, with a brush, in a single layer of 150 μm, to a clean and dry area of skin of 3 cm$^2$.

The area of skin covered is then continuously exposed, under air and at ambient temperature, to UV-visible radiation having a wavelength of 385 nm emitted by an LED-LC3 (Hamamatsu Photonics K.K.) positioned at a distance of 7.5 cm from the area of skin and with a surface power density of 0.1603 W·cm$^{-2}$.

After 10 minutes of exposure, the skin is covered with a polymerized film which is elastic, which adheres to the skin for several hours, which does not exhibit any surface tackiness, which withstands water, in particular withstands several washings of the hands, and which has good breaking strength.

Moreover, the photopolymerizable liquid composition of examples 1, 2 and 3 was applied, with a brush, in a single layer, to a clean and dry area of skin of 3 cm$^2$.

The area of skin covered is then continuously exposed, under air and at ambient temperature, to an LED-LZ1 lamp having a wavelength of 385 nm and a strength of 200 mA at a distance of 2 cm from the skin for 2 minutes.

The persistence over time of the formula according to example 1 was on average 18 hours, that of example 2 was on average 6 hours and that of example 3 was on average 28 hours.

The invention claimed is:

1. A method of covering tissue with a polymerized film made from a polymerization liquid composition comprising: at least one epoxidized polybutadiene prepolymer, at least one cationic onium salt photoinitiator, and at least one thioxanthone derivative photosensitizer, wherein said method comprises
   i. applying said composition to said tissue so as to form a uniform liquid film, and
   ii. subjecting the film obtained in step i. to UV-visible radiation having a wavelength of between 380 and 405 nm; and
   wherein said tissue is the skin, the skin appendages or mucous membranes.

2. The method of claim 1 wherein the thickness of the uniform liquid film is greater than 500 nm.

3. The method of claim 1, wherein the film obtained in step i. is subjected to UV-visible radiation, for a period of between 5 seconds and 60 minutes.

4. The method of claim 1 wherein the thickness of the uniform liquid film is between 1 and 300 µm.

5. The method of claim 1 wherein the thickness of the uniform liquid film is between 2 and 200 µm.

6. The method of claim 1, wherein said UV-visible radiation has a wavelength of between 385 and 395 nm.

7. The method of claim 1, wherein the photopolymerizable liquid composition further comprises a second prepolymer.

8. The method of claim 7, wherein the second prepolymer is a vegetable oil of natural origin functionalized with at least one cationically polymerizable epoxide group.

9. The method of claim 7, wherein the second prepolymer is selected from the group consisting of epoxidized almond oil, epoxidized peanut oil, epoxidized argan oil, epoxidized rapeseed oil, epoxidized coconut oil, epoxidized linseed oil, epoxidized corn oil, epoxidized mustard oil, epoxidized olive oil, epoxidized palm oil, epoxidized grapeseed oil, epoxidized castor oil, epoxidized sesame oil, epoxidized soybean oil, epoxidized sunflower oil, and mixtures thereof.

10. The method of claim 1, wherein the photopolymerizable liquid composition further comprises a hydrogen-donor compound.

11. The method of claim 10, wherein the hydrogen-donor compound is a primary, secondary or tertiary alcohol.

12. The method of claim 10, wherein the hydrogen-donor compound is selected from the group consisting of n-propanol, isopropanol, benzyl alcohol, t-butanol, and mixtures thereof.

* * * * *